United States Patent [19]
Sher

[11] Patent Number: 5,556,417
[45] Date of Patent: Sep. 17, 1996

[54] LUMINESCENT EYE FIXATION DEVICE

[75] Inventor: Neal A. Sher, Minneapolis, Minn.

[73] Assignee: EyeFix, Inc., Minneapolis, Minn.

[21] Appl. No.: 216,726

[22] Filed: Mar. 23, 1994

[51] Int. Cl.⁶ .............................. A61F 9/00; A61B 17/02
[52] U.S. Cl. ................................... 600/236; 606/166
[58] Field of Search ......................... 606/166, 4–6, 606/161, 130; 355/76; 600/236

[56] References Cited

U.S. PATENT DOCUMENTS

| | | | |
|---|---|---|---|
| 2,702,540 | 2/1955 | Debeh | 128/20 |
| 3,807,393 | 4/1974 | McDonald | 128/20 |
| 4,052,980 | 10/1977 | Grams et al. | 128/18 |
| 4,226,228 | 10/1980 | Shin et al. | 128/20 |
| 4,412,738 | 11/1983 | Ahern et al. | 355/76 |
| 4,414,979 | 11/1983 | Dotson et al. | 128/305 |
| 4,669,870 | 6/1987 | Fosh | 355/76 X |
| 4,688,571 | 8/1987 | Tesler | 128/360 |
| 4,820,036 | 4/1989 | Seet | 351/156 |
| 4,959,067 | 9/1990 | Muller | 606/190 |
| 5,007,924 | 4/1991 | Jekel | 606/234 |
| 5,009,660 | 4/1991 | Cladham | 606/166 |
| 5,035,232 | 7/1991 | Lutze et al. | 128/20 |
| 5,070,860 | 12/1991 | Grounauer | 128/20 |
| 5,159,921 | 11/1992 | Hoover | 128/20 |
| 5,171,254 | 12/1992 | Sher | 606/166 |
| 5,189,445 | 2/1993 | Stagner | 351/46 |
| 5,330,492 | 7/1994 | Haugen | 606/167 |

OTHER PUBLICATIONS

Material Safety Data Sheet entitled "Glo–in–the–Dark Phosphorescent—Pigment P1000," distributed by Hanovia, Newark, New Jersey, Jan. 1, 1992, five pages.

Primary Examiner—Michael H. Thaler
Assistant Examiner—Nancy Mulcare
Attorney, Agent, or Firm—Gregory P. Kaihoi; Edward S. Hotchkiss

[57] ABSTRACT

A phosphorescent ophthalmic instrument for fixating a patient's eye during an ophthalmic procedure. The instrument includes a fixation structure attachable to the patient's eye, at least a portion of the fixation ring being made from a phosphorescent material. This material, visible to the physician after exposure to incident visible light when substantially all room (and operating) lights are turned off, enables the physician to visualize the location of the fixation ring in a dark operating environment.

17 Claims, 2 Drawing Sheets 5,556,417

LUMINESCENT EYE FIXATION DEVICE

FIELD OF THE INVENTION

The invention relates to an eye fixation device useful in restraining movement of an eye during ophthalmic procedures.

BACKGROUND OF THE INVENTION

In a variety of surgical procedures on the eye, it is desirable or necessary to prevent the eye from moving. Examples include corneal refractive surgery, corneal laser surgery (e.g., with the 193 nm excimer laser), and radial keratotomy. Currently, ophthalmologists use one of a variety of types of instruments to stabilize the eye during such procedures.

One such device is shown in U.S. Pat. No. 5,009,660 (Clapham). The Clapham device utilizes a vacuum ring carded at the end of a handle which extends away from the vacuum ring at an angle. The vacuum ring can be secured to the eye around the cornea, permitting the physician to substantially prevent movement of the eye.

U.S. Pat. No. 4,718,418 (L'Esperance) uses a vacuum ring which can be placed on the eye, the vacuum ring being rigidly connected to an external piece of equipment (in this case, a laser used in treatment of the eye).

My prior patent, U.S. Pat. No. 5,171,254, shows an eye fixation device that includes a speculum securable against the patient's bony orbit, and a separate fixation ring attachable to the patient's eye (typically by vacuum). A mechanism is provided for adjustably attaching the ring to the speculum to prevent movement of the eye once the proper position of the eye for the procedure is obtained.

In some ophthalmic procedures, such as corneal excimer laser surgery, it is desirable to first remove the epithelium layer of the cornea. This can be accomplished by merely mechanically scraping this thin layer off with a suitable device. Alternately, in an excimer laser procedure the laser itself can be used to remove the epithelial layer. This layer is of varying thickness of different patients, however, and its thickness (typically on the order of about 45–55 microns) is not easy to measure. Thus, it can be difficult to estimate the length of time necessary for the laser to remove just this thin layer.

It has been discovered, however, that epithelial cells of the human cornea fluoresce (green) when exposed to the 193 nm light of the excimer laser. Thus, with the operating room lights turned off, the physician can observe this fluorescence as the laser ablates the epithelium, arid can stop the laser ablation when the fluorescence disappears. With all room lights turned off, however, it can be difficult for the physician to monitor the position of the eye just before turning the laser on and when the epithelium has been nearly entirely ablated; it is also difficult to confirm that the eye has not moved during the procedure.

SUMMARY OF THE INVENTION

The invention provides a phosphorescent fixation device for securing a patient's eye during an ophthalmic procedure. The fixation device includes a fixation structure including means for fixating such structure with respect to the eye (such as by vacuum), at least a portion of the fixation structure including phosphorescent material visible to the physician when substantially all room lights are turned off.

In a preferred embodiment, the device includes a speculum for holding the patient's eyelid open, the speculum seating against the bony orbit of the eye, and an associated fixation ring including means for fixating the ting with respect to the eye (such as by vacuum), the fixation ring being at least partially made of or including phosphorescent material. Means is provided for adjustably securing the ring to the speculum.

In use, the speculum is inserted against the eyelids, and seated against the bony orbit. The fixation ring is then positioned concentrically around the cornea (typically seating on the episclera). The physician then has the patient look directly at a target (to properly align the eye, e.g. with respect to a laser or other operating device), and the fixation ring is then firmly secured to the speculum to immobilize the eye.

Preferably the fixation structure is molded from a plastic polymer, and the phosphorescent material is integrally contained in such polymer. Alternately, the phosphorescent material may be applied to a surface of the fixation structure. In a preferred embodiment the phosphorescent material is shaped and/or positioned so as to provide radial markings visible to the physician indicating the rotational orientation of the fixation structure. Such markings could be provided either by strategically placing the phosphorescent material in certain locations, or by covering selected portions of the phosphorescent material with opaque markings.

BRIEF DESCRIPTION OF THE DRAWINGS

FIG. 2b is an enlarged detail of an alternative embodiment of the structure of FIG. 2a.

BEST MODE FOR CARRYING OUT THE INVENTION

Figure 1:
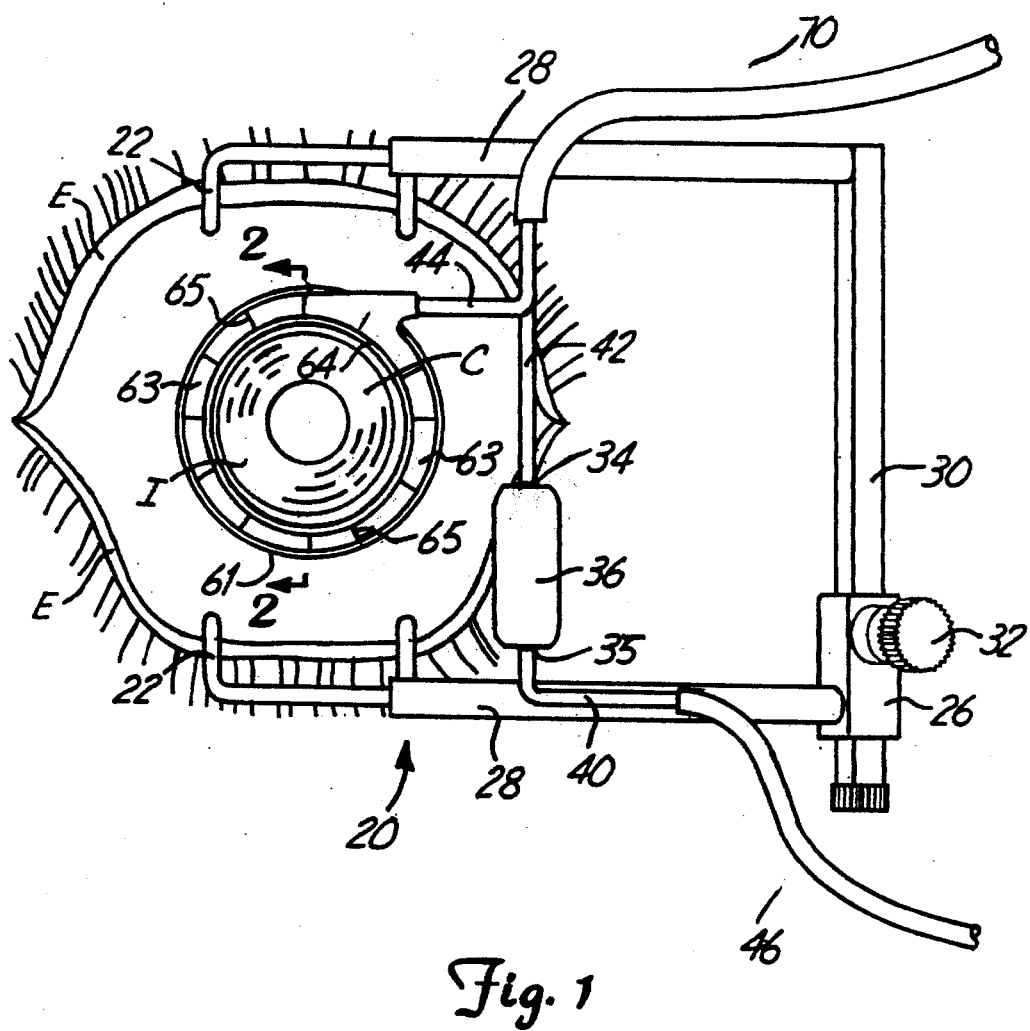
FIG. 1 is a top, plan view of the device secured to the eye of a patient.

The fixation device of the invention includes a speculum 20 have a pair of opposed retractors 22 for holding the eyelids E open against the bony orbit of a patient. The retractors 22 are carried by a pair of arms 28 (or equivalent structure) which in turn are secured to one another in a fashion so as to provide adjustability and to securely hold the eyelid open against the bony orbit. A spring mechanism, similar to that described in my earlier patent (U.S. Pat. No. 5,171,254, which is hereby incorporated by reference) may be utilized. Alternately, as shown in FIG. 1, one of the arms 28 may be connected to a generally perpendicularly oriented frame member 30, with the other arm 28 being mounted to a slidable collar 26 which may be moved to adjust the distance between the retractors 22 to accommodate varying eye sizes. The collar 26, when properly positioned, may be secured to the frame member in any suitable fashion, such as by tightening set screw 32. Any other suitable biasing mechanism may be used to provide the requisite force for holding the retractors 22 against the bony orbit B.

Figure 2:
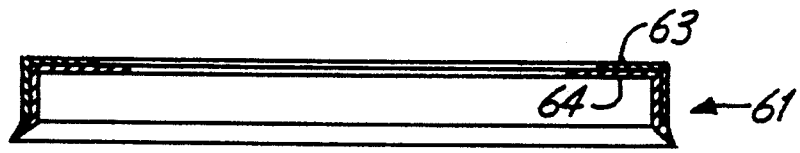
FIG. 2 is a cross-sectional view of FIG. 1 taken along line 2—2 thereof.
Figure 2A:
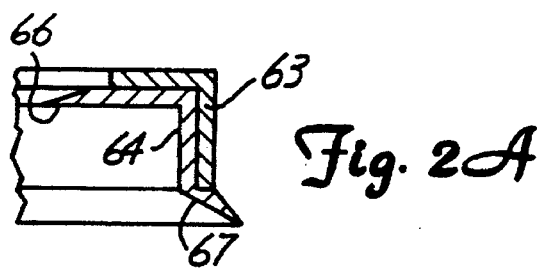
FIG. 2a is an enlarged detail of the right side of FIG. 2.
Figure 2B:
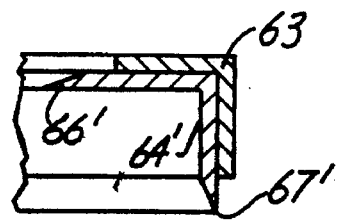

The fixation ring carded by the speculum includes an annular fixation portion 61 which is to be positioned concentrically about the cornea C of the eye. As shown in FIGS. 2, 2a and 2b, preferably the fixation portion 61 includes a relatively rigid outer support ring 63 and an inner, relatively flexible ring 64 for engagement with the cornea C of the eye. The inner and outer rims 66 and 67, respectively, of the flexible ring 64 engage the surface of the cornea C, thereby defining with the surface of the cornea a cavity in which a vacuum can be drawn to secure the device to the eye. FIG. 2b shows a slight variation on the configuration of the flexible ring 64'. Other suitable configurations may also be utilized. The vacuum portion of the ting 61 communicates with vacuum tube 70 through support arm 44. Any suitable vacuum source may be utilized, such as a large syringe with a spring plunger, or other suitable vacuum supply.

Figure 3:
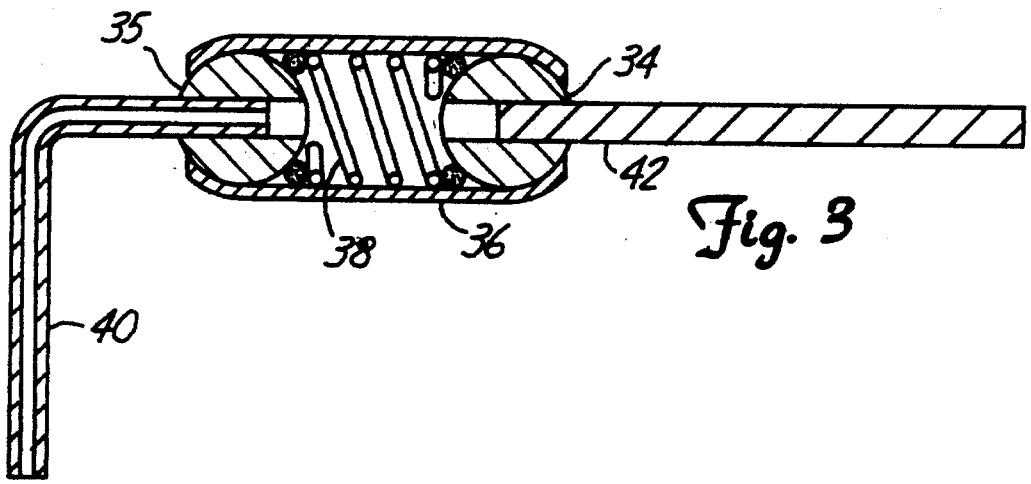
FIG. 3 is a cross-sectional, partially broken-away view of the ball valve and housing shown in FIG. 1.

Means is provided for fixating the ring 61 with respect to the speculum 20. In a preferred embodiment illustrated in the drawings, the ring is connected by supporting arm 44 to connecting arm 42, which in turn is adjustably connected to retractor arm 28 by way of a double ball-type valve linkage. This linkage is shown in greater detail in FIG. 3. A generally cylindrical housing 36 contains a pair of balls 35 which are closely received in opposite tapered ends of the housing 36. When there is no air pressure differential between the interior and the exterior of the housing, the balls are free to rotate within the housing, providing for adjustable orientation of the fixation ring 61. When air pressure is supplied to the housing through supply tube 46 and inlet tube 40 (which is rigidly connected to speculum arm 28), the balls are urged out into firm sealing contact with the complimentary end portions of the housing 36, thereby substantially immobilizing the ring 61 with respect to the speculum 20. A spring 38 is provided to keep the balls positioned at their respective ends of the housing. Alternate equivalent means could also be employed to secure the fixation ring 60 to the speculum 20.

Phosphorescent material is provided at least on or in a visible surface of the fixation ting 61. Preferably the fixation ring 61 (or the equivalent structure of a device similar to the preferred embodiment illustrated in the drawings) is molded from a plastic or rubber polymer,, with the phosphorescent material being integrally contained in such polymer. (In the embodiments shown in the drawings, the phosphorescent material could be contained in either the rigid ring 63 or in the flexible ring 64, or both.) Alternately, the phosphorescent material may be applied (in, e.g., the form of paint, decals, or otherwise) to the surface of the fixation ring. In a preferred embodiment the phosphorescent material is shaped and/or positioned so as to provide radial markings visible to the physician indicating the rotational orientation of the fixation structure. Such markings could be provided either by strategically placing the phosphorescent material in certain locations, or by covering selected portions of the phosphorescent material with opaque markings, such as radial markings 65 in FIG. 1.

Any of a variety of types of phosphorescent material will work well in the present invention. The material need only to continue to emit visible light after all room lights and operating microscope lights have been turned off. It has been found that integrally molding combinations of zinc sulfide and zinc oxide with polymer resin used to mold the fixation ring gives good results. One commercially available zinc oxide/zinc sulfide mixture that has worked well is Hanovia P1000000 (available from Hanovia, an ARC International Company, 100 Chestnut Street, Newark, N.J.). This material is non-toxic, non-radioactive, and generally bio-compatible, giving off a yellow-green color.

Suitable resins for molding the device of the invention include thermoplastics, such as C-Flex R70-028 35A (available from Concept Polymer Technologies, Inc., 8625 Bryan Dairy Road, Largo, Fla. 34647) and medical grade silicone rubbers, such as MDX-4-4515 and MDX-4-4516 (50 and 70 durometer, respectively, medical grade silicone rubber available from Dow Coming Corporation, Midland, Mich. 48640).

When the phosphorescent material is integrally contained in the polymer ring, it has been found that concentrations of the above-identified P1000000 material work well in the range of about 20%. Optimal concentration will depend on the color of the polymer resin, the performance of the phosphorescent material being used, and the "brightness" (i.e., level of phosphorescence) desired. Using the materials identified above, less than 5% (by weight) of the P1000000 material does not generally produce sufficient phosphorescence, and concentrations significantly in excess of about 20% tend to make the resultant product more friable.

In use, the physician first locates the patient in the position for the procedure, such as laying prone. The speculum 20 is then inserted to hold the eyelids E open, the speculum being seated against the bony orbit B of the patient. The fixation ring 60 is then placed on and centered on the eye about the cornea C so that it is generally coaxial of the cornea. Typically the ring 61 will actually rest on the episcleral/conjunctival surface near the limbus. The fixation ring is secured to the eye by actuation of vacuum attached to the vacuum tube 70. The physician then asks the patient to look directly at a point of light or similar target to properly orient the patient's eye with respect to the laser or other instrument to be utilized by the physician. When the physician determines that the alignment is proper, the attachment means between the speculum and the fixation ring is actuated (as by supplying air pressure to the ball valve linkage by actuating a syringe connected to tube 46, or by other suitable means). The fixation ring 61 is thereby secured to the speculum to substantially immobilize the patient's eye for the procedure to be performed.

Room lights may then be turned off to enable the physician to monitor the disappearance of fluorescence of the epithelial cells as the laser ablates them. When room lights are turned off, the phosphorescence of the ting 61 enables the physician to easily focus his attention directly at the cornea, even though the cornea itself is not visible until (and to the extent that) the laser causes the epithelial cells to fluoresce. The physician is thus more easily able to confirm that the patient's eye continues to be properly positioned under the laser and does not substantially move during removal of the epithelium. It will be appreciated that although the invention has been compatible with respect to a particular eye fixation device, other configurations of ocular fixation devices, hand-held or otherwise, can also advantageously utilize the fluorescent ring of the invention.

The device of the invention can be manufactured from any suitable materials. Desirably, the device can be made of suitable plastics and/or metals and can be cheaply manufactured so as to be disposable, thereby eliminating the need for repeat sterilization. Preferably the speculum is made of stainless steel, while the fixation ring is molded from suitable polymer resins, such as those discussed above. Both the speculum and the fixation ting can also be manufactured in different diameters for use in different sized eyes. If desired, the bottom surface of the fixation ring can be made out of silicone to assure a good seal against the eye and to minimize any trauma to the ocular surface.

While a preferred embodiment of the present invention has been described, it should be understood that various changes, adaptations and modifications may be made therein without departing from the spirit of the invention and the scope of the appended claims.

What is claimed is:

1. An ophthalmic instrument for fixating a patient's eye during an ophthalmic procedure, comprising a fixation structure adapted to engage a surface of the eye adjacent the cornea, at least a portion of the fixation structure including phosphorescent material visible to a physician in the dark, thereby enabling the physician to visualize the location of the ophthalmic instrument as a point of reference which can be used in a dark operating environment to determine the relative location of the cornea.

2. The instrument of claim 1 wherein the fixation structure comprises a fixation ring.

3. The instrument of claim 1 wherein the fixation structure further comprises vacuum means associated therewith for securing the fixation structure to the surface of the eye.

4. The instrument of claim 1 wherein the fixation structure is made from a plastic polymer, the phosphorescent material being integrally contained with such plastic polymer.

5. The instrument of claim 1 wherein the phosphorescent material is applied to a surface of the fixation structure.

6. The instrument of claim 1 wherein the phosphorescent material is shaped and positioned so as to provide markings visible to the physician indicating the rotational orientation of the fixation structure.

7. The instrument of claim 1 wherein the fixation structure further comprises a vacuum source and passageways defined in the fixation structure for communicating the vacuum source with a bottom surface of the fixation structure securable against the patient's eye.

8. An ophthalmic instrument for fixating a patient's eye during an ophthalmic procedure, comprising:

a speculum securable against the patient's bony orbit, the speculum including a pair of opposed retractors for engaging the patient's eyelid against the patient's bony orbit, and means for biasing the retractors away from one another;

a fixation ring adapted to engage a surface of the eye adjacent the cornea and comprising a vacuum source and passageways defined in the fixation ring for communicating the vacuum source with a bottom surface of the ring securable against the patient's eye; and attachment means for adjustably attaching the ring to the speculum;

at least a portion of the fixation ring being made from a phosphorescent material visible to the physician in the dark after exposure to incident visible light, thereby enabling the physician to visualize the location of the fixation ring as a point of reference which can be used in a dark operating environment to determine the relative location of the cornea.

9. An ophthalmic instrument for fixating a patient's eye during an ophthalmic procedure, comprising a speculum and a fixation ring attached to the speculum, the speculum having opposed retractors for holding a patient's eyelid away from the patient's cornea, the fixation ring being sized and shaped to engage a surface of the patient's eye adjacent the patient's cornea, at least a portion of the fixation ring being phosphorescent so the phosphorescent portion defines a visible point of reference which can be used in a dark operating environment to determine the relative location of the patient's cornea.

10. The ophthalmic instrument of claim 9 wherein the fixation ring comprises a vacuum source and an annular ring having a bottom surface and a passageway therein for communicating the vacuum source with the bottom surface and the patient's cornea.

11. The ophthalmic instrument of claim 9 wherein the fixation ring comprises phosphorescent material sized and positioned to provide markings visible to the physician indicating the rotational orientation of the fixation ring.

12. The ophthalmic instrument of claim 11 wherein the fixation ring is generally annular in shape and the markings comprise phosphorescent material applied to a surface of the fixation ring to extend generally radially on said surface.

13. The ophthalmic instrument of claim 11 wherein the fixation ring is made from a plastic polymer, the phosphorescent material being integrally contained in said plastic polymer, and the markings comprise opaque markings applied to a surface of the fixation ring.

14. The ophthalmic instrument of claim 13 wherein the fixation ring is generally annular in shape and the opaque markings extend generally radially along said surface.

15. A method of operating on a patient's eye, comprising the steps of:

a. providing a fixation structure adapted to engage a surface of the eye, at least a portion of the fixation structure being phosphorescent;

b. in an operating environment, attaching the fixation structure to the surface of the eye to fixate the eye, in a selected position;

c. darkening the operating environment and, in the dark operating environment, monitoring the position of the phosphorescent fixation structure as a point of reference for monitoring the location of the surface of the eye during an ophthalmic procedure.

16. The method of claim 15 further comprising attaching the fixation structure to the surface of the eye adjacent the cornea by means of a vacuum and wherein the position of the fixation structure is monitored during the procedure to monitor the location of the patient's cornea.

17. The method of claim 15 wherein the phosphorescent portions of the fixation structure define visible markings indicating the rotational orientation of the fixation structure, the step of monitoring the position of the fixation structure further comprising monitoring the positions of the markings to monitor the rotational orientation of the surface of the eye.

* * * * *